US011446446B2

(12) United States Patent
McLusky et al.

(10) Patent No.: US 11,446,446 B2
(45) Date of Patent: Sep. 20, 2022

(54) ACCESSORY FOR AN INJECTION DEVICE INCLUDING A GRIP FOR A NEEDLE CAP

(71) Applicant: Janssen Pharmaceuticals, Inc., Titusville, NJ (US)

(72) Inventors: James D. McLusky, Edinburgh (GB); Nick Foley, Edinburgh (GB); Gavin F. McDougall, Edinburgh (GB); Roy A. Crerar, Edinburgh (GB); James N. Mower, Edinburgh (GB)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 219 days.

(21) Appl. No.: 16/716,938

(22) Filed: Dec. 17, 2019

(65) Prior Publication Data
US 2020/0197623 A1 Jun. 25, 2020

(30) Foreign Application Priority Data

Dec. 21, 2018 (GB) ..................................... 1821073

(51) Int. Cl.
*A61M 5/32* (2006.01)
*A61M 5/31* (2006.01)
(52) U.S. Cl.
CPC ........ *A61M 5/3204* (2013.01); *A61M 5/3213* (2013.01); *A61M 2005/3139* (2013.01)
(58) Field of Classification Search
CPC .................................................. A61M 5/3204
See application file for complete search history.

(56) References Cited

U.S. PATENT DOCUMENTS

| 8,313,470 | B2 | 11/2012 | Abry |
| 8,608,707 | B2 | 12/2013 | Abry |
| 8,708,968 | B2 | 4/2014 | Julian et al. |
| 8,814,828 | B2 | 8/2014 | Llewellyn-Hyde et al. |
| 8,992,477 | B2 | 3/2015 | Raday et al. |

(Continued)

FOREIGN PATENT DOCUMENTS

| EP | 1948269 A1 | 4/2007 |
| EP | 2211944 A1 | 4/2009 |

(Continued)

OTHER PUBLICATIONS

International Search Report dated Mar. 3, 2020; International Application No. PCT/IB2019/060974.

(Continued)

*Primary Examiner* — Emily L Schmidt
(74) *Attorney, Agent, or Firm* — Craig M. Brown

(57) ABSTRACT

An accessory for an injection device having a needle cap. The accessory comprises a body portion comprising a recess adapted to receive the injection device and a cover coupled to the body portion. The cover is pivotally moveable between an open position in which the recess is exposed to receive the injection device, and a closed position in which the cover at least partially closes the recess to hold the injection device in the body portion. The accessory further comprises a cap remover comprising a grip, the cap remover having an expanded configuration in which the needle cap can pass between the grip, and a constricted configuration in which the grip holds the needle cap to at least partially remove the needle cap from the injection device.

26 Claims, 16 Drawing Sheets

(56) References Cited

U.S. PATENT DOCUMENTS

| | | |
|---|---|---|
| 9,233,212 B2 | 1/2016 | Holmqvist |
| 9,242,050 B2 | 1/2016 | Abry |
| 9,339,610 B2 | 5/2016 | Julian et al. |
| D784,526 S | 4/2017 | Grunhut |
| D784,527 S | 4/2017 | Llewellyn-Hyde |
| D785,163 S | 4/2017 | Nakamura et al. |
| D785,788 S | 5/2017 | Nguyen |
| D787,664 S | 5/2017 | Grunhut |
| 9,656,026 B2 | 5/2017 | Bostrom |
| 9,931,474 B2 | 4/2018 | Holmqvist |
| D819,805 S | 6/2018 | Knight et al. |
| 10,022,503 B2 | 7/2018 | Julian et al. |
| D849,935 S | 5/2019 | Rolfs et al. |
| 2007/0239117 A1 | 10/2007 | Chelak et al. |
| 2008/0228147 A1 | 9/2008 | David-Hegerich et al. |
| 2008/0269692 A1 | 10/2008 | James et al. |
| 2008/0300549 A1 | 12/2008 | Verespej et al. |
| 2013/0085446 A1 | 4/2013 | Pellegrini et al. |
| 2014/0364805 A1 | 12/2014 | Llewellyn-Hyde et al. |
| 2015/0051578 A1 | 2/2015 | Herr |
| 2015/0196714 A1 | 7/2015 | Creaturo |
| 2015/0202379 A1 | 7/2015 | Raday et al. |
| 2015/0297833 A1* | 10/2015 | Henderson .......... A61M 5/3129 604/135 |
| 2016/0184531 A1* | 6/2016 | Schiller .................. A61M 5/28 604/506 |
| 2017/0014578 A1 | 1/2017 | Bunch |
| 2017/0173270 A1* | 6/2017 | Nakamura .......... A61M 5/3257 |
| 2017/0274152 A1 | 9/2017 | Bostrom |
| 2017/0354789 A1 | 12/2017 | Bendek |
| 2017/0361030 A1 | 12/2017 | Moore |

FOREIGN PATENT DOCUMENTS

| | | |
|---|---|---|
| EP | 2361648 A1 | 8/2011 |
| EP | 2667914 A1 | 8/2012 |
| EP | 2667915 A1 | 8/2012 |
| EP | 2727617 | 5/2014 |
| EP | 2203204 B1 | 12/2014 |
| EP | 2923716 A1 | 9/2015 |
| EP | 3122403 A1 | 10/2015 |
| EP | 2768560 B1 | 9/2016 |
| EP | 2873431 B1 | 7/2017 |
| EP | 3241583 A1 | 11/2017 |
| EP | 3257536 A1 | 12/2017 |
| EP | 3257540 A1 | 12/2017 |
| EP | 2729203 B1 | 1/2018 |
| FR | 3025433 | 4/2016 |
| GB | 2563027 | 12/2018 |
| GB | 2563029 | 12/2018 |
| JP | 3143302 | 7/2008 |
| JP | 2011098133 | 5/2011 |
| JP | 5211167 | 6/2013 |
| JP | 5216859 | 6/2013 |
| JP | 2015208567 | 11/2015 |
| JP | 5968914 | 8/2016 |
| JP | 6200558 | 9/2017 |
| JP | 2017221731 | 12/2017 |
| JP | 2018196649 | 12/2018 |
| WO | WO 2009/040601 | 4/2009 |
| WO | WO 2009/040603 | 4/2009 |
| WO | WO 2012/101629 | 8/2012 |
| WO | WO 2012/103140 | 8/2012 |
| WO | WO 2013/006119 | 1/2013 |
| WO | WO 2013/058697 | 4/2013 |
| WO | WO 2014/072237 | 5/2014 |
| WO | WO 2014/144096 | 9/2014 |
| WO | WO 2015/122884 | 8/2015 |
| WO | WO 2015/144871 | 10/2015 |
| WO | WO 2017/089264 | 6/2017 |
| WO | WO 2017/089266 | 6/2017 |
| WO | WO 2017/089283 | 6/2017 |
| WO | WO 2017/179638 | 10/2017 |

OTHER PUBLICATIONS

International Search Report dated May 6, 2020; International Application No. PCT/IB2019/060975.

International Search Report dated Mar. 3, 2020; International Application No. PCT/IB2019/060976.

International Search Report dated May 7, 2020; International Application No. PCT/IB2019/060980.

* cited by examiner

ACCESSORY FOR AN INJECTION DEVICE INCLUDING A GRIP FOR A NEEDLE CAP

CROSS-REFERENCE TO RELATED APPLICATIONS

This application claims priority under 35 U.S.C. Section 119 to GB Application No. 1821073.2, filed on Dec. 21, 2018, which is incorporated by reference herein in its entirety.

TECHNICAL FIELD

This disclosure relates to an accessory for an injection device.

BACKGROUND

Needle safety devices are commonly used in combination with syringes when performing injections, in order to reduce the risk of accidental needle sticks which can result in transmission of blood borne pathogens. These needle safety devices are typically required to protect Health Care Providers (HCPs), such as nurses, who frequently use syringes to administer injections to patients. Needle safety devices typically can be categorised as one of two types: (1) passive devices that automatically cover the needle after the injection, without requiring additional steps from the user in order to activate the device; and (2) devices that require an additional step by the user in order to activate the needle safety feature.

Passive needle safety devices generally are considered to be superior in their ability to protect the user from accidental needle sticks, because, for various reasons, users may fail to take the additional actions required to activate non-passive devices. Health authorities and health care systems often require the use of needle safety devices in settings where HCPs perform injections. Furthermore, needle safety devices are desirable for self-administered and caregiver-administered injections to mitigate the risk of injury, infection, and the spread of blood borne pathogens to patients, family members, caregivers and anyone who might come in contact with the injection devices in the process of performing the injection and disposing of used syringes.

A commonly used example of needle safety devices is the UltraSafe™ family of devices, manufactured by Becton Dickinson. The UltraSafe™ consists of two plastic components and a spring that are assembled to the syringe, along with a custom plunger rod. Upon completion of the injection, the plunger rod engages latches on the UltraSafe™ housing components, activating the device and causing the spring to extend one of the housing components over the needle and lock into place, into a locked-out position. An example of an UltraSafe™ device is shown in FIGS. 1A and 1B.

FIG. 1A shows the device in a ready state before an injection takes place, or in a pre-injection position. FIG. 1B shows the device in a safe, used state, after an injection has been completed, or in a locked-out position.

FIGS. 2A, 2B, 2C, and 2D show the typical instructions for using the UltraSafe™ device. As can be seen, the steps for using the UltraSafe™ are essentially the same as for performing an injection with a bare syringe. Pinching the skin and injecting at a 45 degree angle are essential to limit the depth of injection and ensure that the injection is given subcutaneously and not into the muscle (too deep) or intradermally (into the skin). Injecting too shallow or too deep can impact the pharmacokinetics (PK) and pharmacodynamics (PD) for drugs that are intended for subcutaneous injection.

As shown in FIGS. 2A-2D, the steps for proper use of a syringe to achieve a subcutaneous injection are complex, and variation from user to user can result in differences in the depth of injection, which can impact the efficacy of the drug. HCPs such as nurses are quite familiar and practiced with the procedure for performing injections with syringes. However, technique does vary from nurse to nurse, which can impact PK and PD. Moreover, the typical injection technique requires the use of two hands, one to pinch and one to inject, making it difficult for nurses to perform the injection on difficult patients such as pediatrics who may move during the injection. Furthermore, even though the nurse is comfortable using a syringe, patients are often scared of the syringe and needle, and the injection often results in an unpleasant patient experience.

Syringes, including the UltraSafe™, are especially difficult for patients and caregivers to use, not only because of the complexity of the use steps, but also because syringes with exposed needles tend to cause anxiety for the patient. Thus, there is a need to develop an accessory that allows a needle safety device, for example such as the UltraSafe™, to be operated more easily.

SUMMARY

In one aspect of the invention, there is provided an accessory for an injection device having a needle cap, the accessory comprising: a body portion comprising a recess adapted to receive the injection device; a cover coupled to the body portion, the cover pivotally moveable between an open position in which the recess is exposed to receive the injection device, and a closed position in which the cover at least partially closes the recess to hold the injection device in the body portion; and a cap remover comprising a grip, the cap remover having an expanded configuration in which the needle cap can pass between the grip, and a constricted configuration in which the grip holds the needle cap to at least partially remove the needle cap from the injection device; wherein the cover and the cap remover are operably coupled to one another so that when the cover is moved from the open position towards the closed position the cap remover moves from the expanded configuration to the constricted configuration.

In this way, the injection device can be loaded into the accessory without the grip interfering with the needle cap. Then, when the cover is closed the grip closes on the needle cap in order to remove the needle cap automatically. Also, after the cover is removed, the grip opens again to release the cover so it can be separated from the accessory.

In another aspect of the invention, there is provided an accessory for an injection device having a needle cap, the accessory comprising: a body portion comprising a recess adapted to receive the injection device; a cover coupled to the body portion, the cover pivotally moveable between an open position in which the recess is exposed to receive the injection device, and a closed position in which the cover at least partially closes the recess to hold the injection device in the body portion; and a cap remover comprising a grip adapted to hold the needle cap, the cap remover being moveable with respect to the body portion, wherein the cover comprises: a proximal end adapted to be moved by a user to move the cover from the open position to the closed position; and a distal end being adapted to move the grip towards an end of the accessory when the cover is moved from the open position to the closed position to at least partially remove the needle cap from the injection device.

In this way, it is possible for the needle cap to be removed automatically when the cover is closed. This is achieved by the cover acting as a lever in order to move the cap remover which causes the needle cap to be removed. This provides a simple and reliable mechanism for removing the needle cover in such a way that users with limited dexterity would find easy. In addition, the cover provides mechanical advantage for moving the cap remover in order to reduce the amount of force required to be provided by the user.

In another aspect of the invention, there is provided an accessory for an injection device having a safety shield and at least one flange adapted to allow a user to grip the injection device and a syringe sheath moveable relative to the at least one flange from a pre-injection position to a locked-out position, the accessory comprising: a body portion comprising a recess adapted to receive the safety shield of the injection device and a slot adapted to receive the at least one flange of the injection device; and a cover coupled to the body portion, the cover pivotally moveable between an open position in which the recess and the slot are exposed to receive the safety shield and the flange of the injection device respectively, and a closed position in which the cover at least partially closes the recess and the slot to hold the injection device in the body portion; wherein the slot is shaped both to resist the at least one flange from moving distally and proximally relative to the body portion and to allow the syringe sheath to move proximally relative to the body portion from the pre-injection position to the locked-out position.

In this way, the cover can be opened in order to allow the recess and the slot to be accessed more easily. Then, when the cover is closed, the slot holds the flange in place, but allows the syringe sheath to move thus not impeding the function of the injection device.

In another aspect of the invention, there is provided an accessory for an injection device having a needle cap, the accessory comprising: a body portion comprising a recess adapted to receive the injection device; a cover coupled to the body portion, the cover pivotally moveable between an open position in which the recess is exposed to receive the injection device, and a closed position in which the cover at least partially closes the recess to hold the injection device in the body portion; and a cap remover comprising a grip adapted to hold the needle cap, the cap remover being moveable axially with respect to the body portion from an initial position to an advanced position to remove the needle cap from the injection device, wherein the body portion comprises a track within which the cap remover is arranged to move axially with respect to the body portion, and wherein the track is adapted such that when the injection device is located in the body portion, the cap remover is held against the track by the injection device.

In this way, the injection device performs the function of holding the needle cap remover inside the track. This avoids the need for additional components which simplifies the design and manufacturing.

The needle cap (equivalently often referred to as a "needle boot" or "needle shield") may be a rigid needle cap or a non-rigid needle cap. The rigid needle cap may be formed of at least two components, for example it may comprise a rigid outer shell and an inner body which surrounds the needle on the syringe when in place. The inner body may be a pliable, resilient or flexible inner body. This inner body may be a rubber inner body. Alternatively, a non-rigid needle cap may be utilised, in which case the needle cap may be a single pliable, resilient or flexible body, for example a rubberised needle boot.

BRIEF DESCRIPTION OF THE DRAWINGS

Embodiments of the invention will be described, by way of example, with reference to the following drawings, in which.

DETAILED DESCRIPTION

Figure 1A:
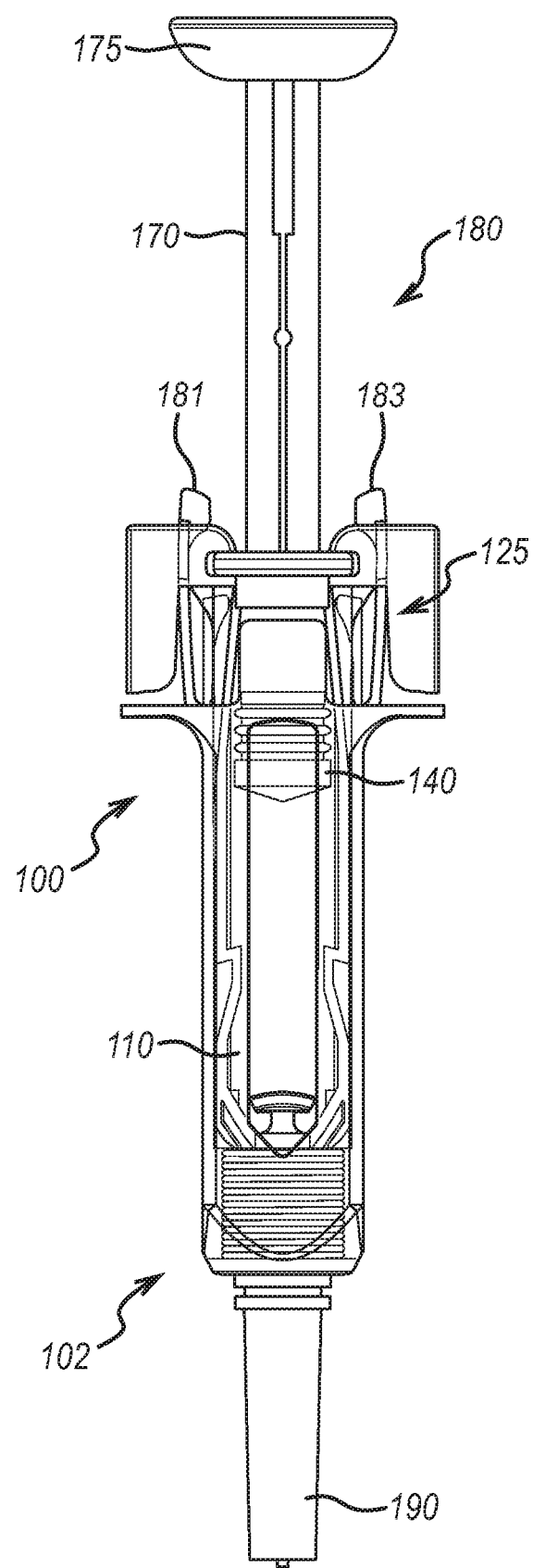
FIGS. 1A-B are perspective views of an injection device in a pre-injection ready state (FIG. 1A), and a safe, locked-out state (FIG. 1B)
Figure 1B:
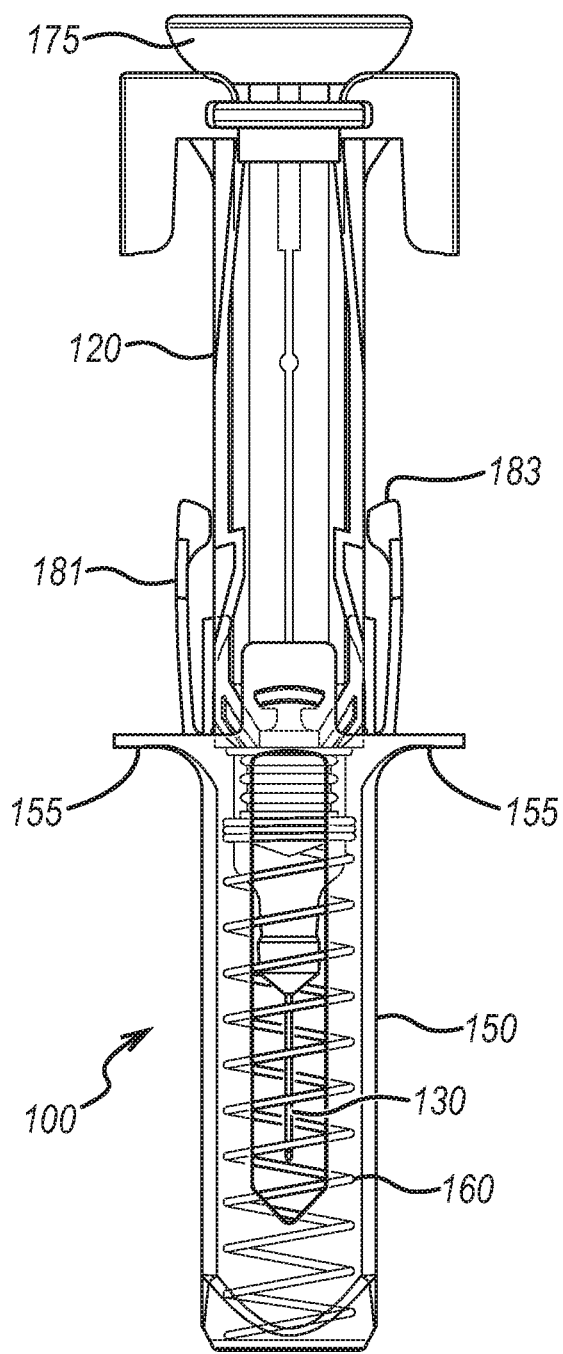
Figure 2A:
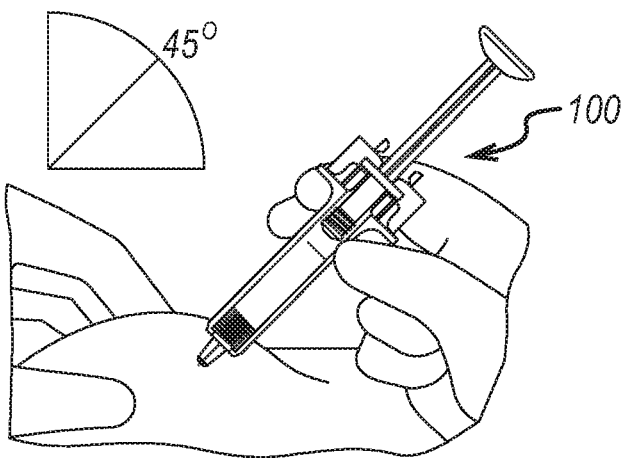
FIGS. 2A-D are example side views depicting use of the injection device of FIG. 1.
Figure 2B:
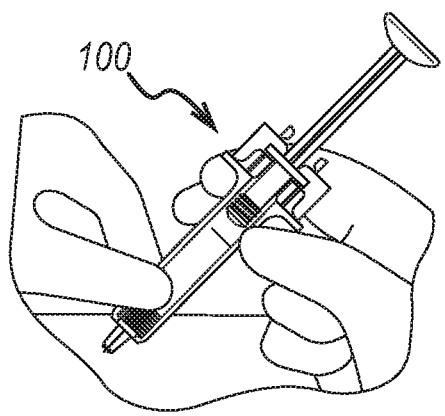
Figure 2C:
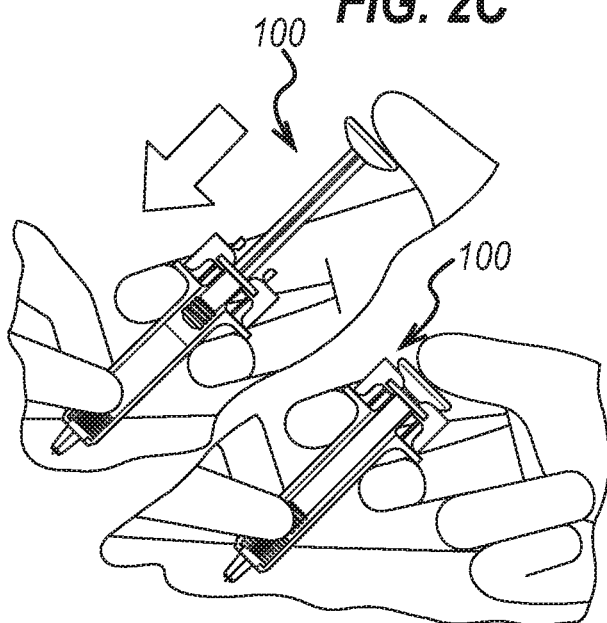
Figure 2D:
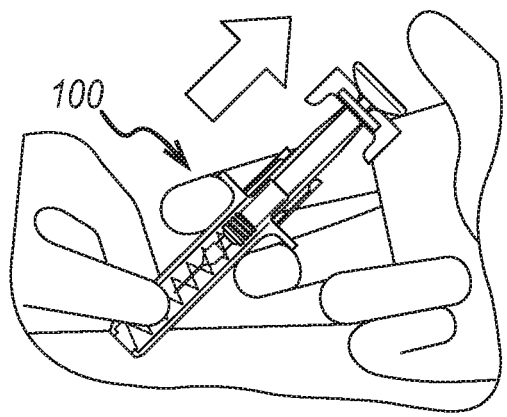

FIGS. 1A-B show a manual injection device 100 that is suitable for use with an accessory of the present disclosure. The injection device 100 comprises a syringe 110, which extends from a distal end comprising a needle 130, to an open proximal end. The open proximal end of the syringe is sealed by a bung 140. A removable needle cap 190 is provided to sheath the needle 130.

The syringe 110 is secured within a syringe sheath 120 by a syringe locking element 125. The syringe locking element 125 may comprise diametrically opposed abutment surfaces between which the flange of a standard syringe is confined. The confinement of the flanges between abutment surfaces prevents movement of the syringe 110 relative to the syringe sheath 120.

The syringe sheath 120 comprises an open proximal end, into which the syringe 110 can be inserted, and an open distal end, from which the needle 130 extends when the syringe 110 is secured within the sheath 120. A safety shield 150 is movably mounted with respect to the syringe sheath 120. The safety shield 150 is movable between a retracted position (shown in FIG. 1A), in which the needle 130 extends beyond the distal end of the safety shield, and an extended position (shown in FIG. 1B), in which the safety shield extends beyond the distal end of the needle 130. In the second position shown in FIG. 1B, the needle 130 is covered by the safety shield 150, thereby shielding the user from the needle and preventing accidental needle-stick injuries.

To allow the user to grip the injection device 100 with a conventional dart grip (as shown in FIG. 2), the safety shield 150 comprises flanges 155 at or towards its proximal end. The flanges 155 shown in FIG. 1 extend from the safety shield 150.

The safety shield 150 is biased into its extended position relative to the syringe sheath 120 (shown in FIG. 1B) by a biasing element 160. The biasing element 160 shown in FIGS. 1A-B takes the form of a coil spring arranged between the syringe sheath 120 and the safety shield 150 such that the safety shield 150 is biased distally relative to the syringe sheath 120 into its extended position.

A releasable locking mechanism 180 retains the safety shield 150 in its retracted position relative to the syringe sheath 120. The locking mechanism 180 is movable between a locked position, in which the locking mechanism 180 prevents the safety shield 150 moving relative to the syringe sheath 120 (FIG. 1A), and an unlocked position in which the locking mechanism 180 no longer prevents movement of the safety shield 150 relative to the syringe sheath 120. Once the locking mechanism is moved to its unlocked position, the safety shield 150 moves to its extended position under the influence of the coil spring 160 (FIG. 1B).

In the device shown in FIGS. 1A-B, the locking mechanism 180 between the safety shield 150 and the syringe sheath 120 takes the form of a pair of flexible latch arms 181 provided on the safety shield 150, which engage opposing latching surfaces 183 on the syringe sheath 120. The flexible latch arms 181 are biased into a first position in which they engage their respective latching surfaces 183, thus preventing distal movement of the safety shield 150 relative to the syringe sheath 120. When the flexible latch arms 181 are moved against this bias, the latch arms 181 disengage their respective latching surfaces 183, thus permitting distal movement of the safety shield 150 relative to the syringe sheath 120.

The latch arms 181 are configured to be moved from the first position to the second position by a plunger rod 170. The plunger rod 170 comprises an elongate member, configured at its distal end to engage the bung 140 and move the bung 140 distally along the longitudinal axis of the syringe body to deliver a dose of medicament through the needle 130. At or towards its proximal end, the plunger rod 170 is provided with an actuation surface 175 on which the user can place a thumb or finger to drive the plunger rod 170 distally to deliver the injection. As the plunger rod 170 nears or reaches the end of its travel within the syringe body, the actuation surface 175 of the plunger rod 170 deflects the flexible latch arms 181 outwardly, to a position in which they no longer engage the latching surfaces 183 on the syringe sheath 120. The locking mechanism is thus released at the end of the injection and the safety shield 150 moves to its extended position.

Although not visible in the accompanying drawings, the manual injection device of FIGS. 1A-B can additionally comprise a safety lock for locking the safety shield 150 in its extended position after the injection has been completed.

Figure 3:
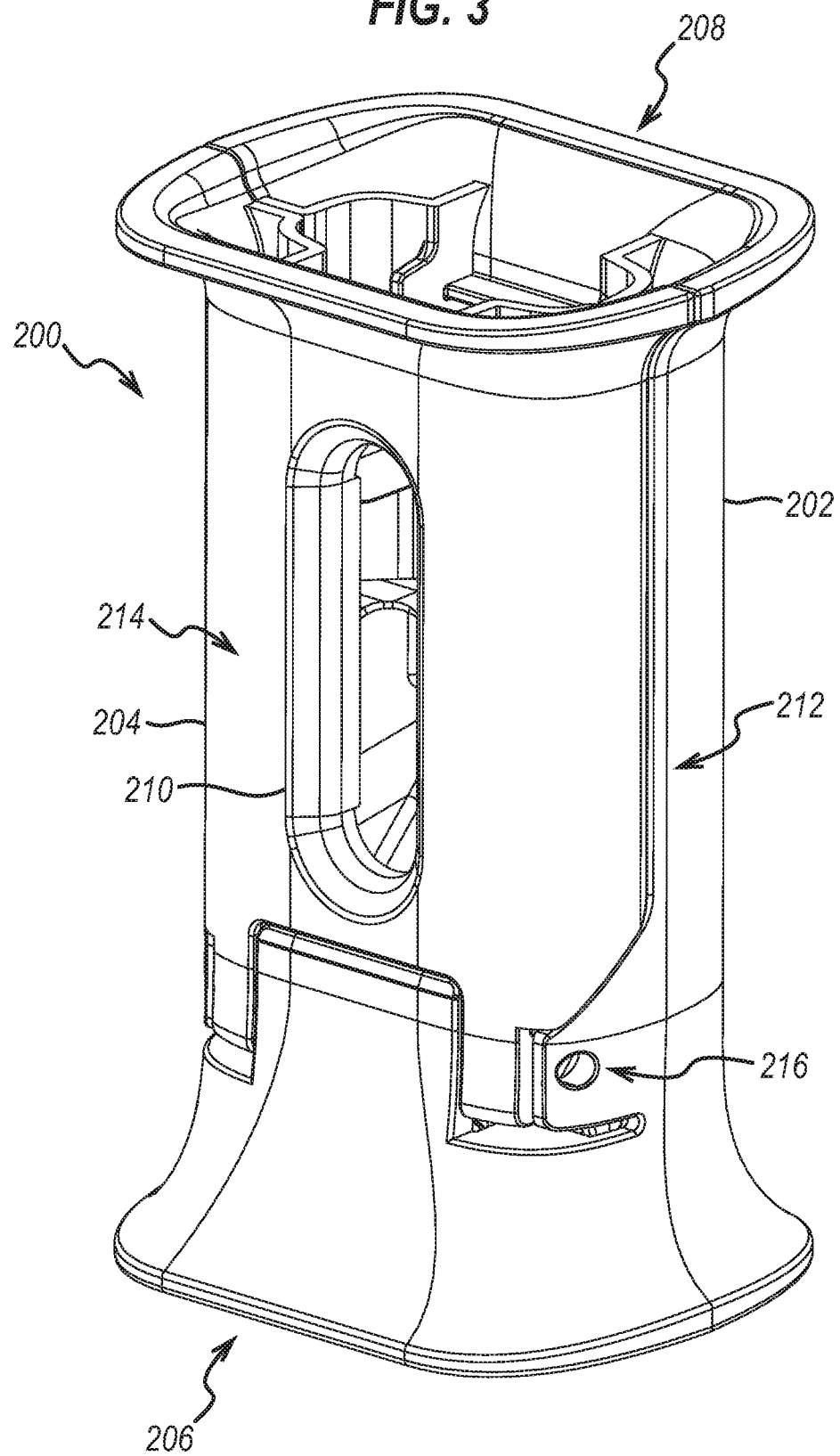
FIG. 3 is a perspective view of an accessory for the injection device, with the accessory in a closed configuration.

Referring to FIG. 3, there is an accessory 200 for use with the injection device 100, such as the UltraSafe™ device. The accessory 200 is described herein using the UltraSafe™ as a specific example of the injection device 100. However, the accessory 200 could be used with other injection devices besides the UltraSafe™ device. For instance, the accessory could be used with the UltraSafe Plus™ device. The structure of the accessory 200 could be modified to conform with the form factor of any suitable injection device.

The accessory 200 comprises a body portion 202 and a cover 204. The accessory 200 has a distal end 206 for positioning towards, or on, an injection site when administering an injection, and a proximal end 208 opposite the distal end 206. The accessory 200 comprises a window 210 in the cover 204. There is also another window in the body 202 on the opposite face of the accessory 200.

Figure 4:
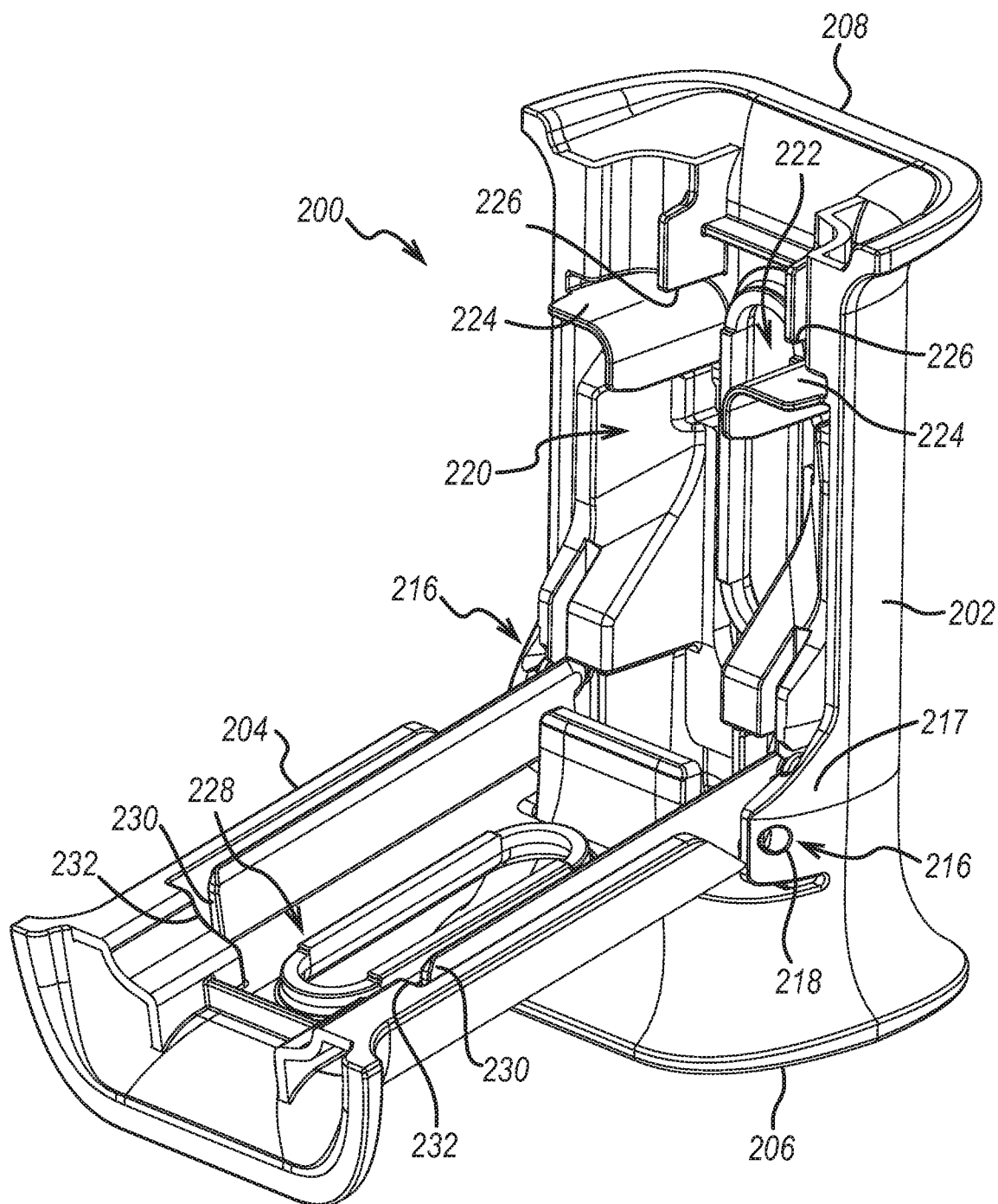
FIG. 4 is a perspective view of the accessory in an open configuration.

Referring to FIG. 4, the cover 204 is coupled to the body portion 202. Specifically, the cover 204 is pivotably coupled to the body portion 202 about a pair of pivots 216. Each one of the pivots 216 is provided towards a respective side of the accessory 200. Each pivot 216 comprises an aperture 218 in the body portion 202 through which a protrusion 203 in the cover 204 passes. Alternatively, the protrusion 203 could be positioned on the body portion 202 with the apertures 218 provided in the cover 204. The protrusion 203 is shown in greater detail in FIGS. 8 and 9. The protrusion 203 is rotatable within the aperture 218 which allows the cover 204 to rotate relative to the body portion 202. In this way, the cover 204 is moveable between an open position, which is the position illustrated in FIG. 4, and a closed position, which is the position illustrated in FIG. 3.

The aperture 218 of each pivot 216 is provided on a resilient attachment member 217 coupled the body portion 202. In this example, the resilient attachment member 217 is integrally formed with the body portion 202. The resilient attachment member 217 is arranged to bend with respect to the body portion 202, so that cover 204 can be inserted between the pivots 216. This simplifies the assembly process. In addition, each protrusion 203 on the cover 204 has a longitudinal surface and a lateral surface. The lateral surface is slanted with respect to the longitudinal surface. In other words, the lateral surface is not perpendicular to the longitudinal surface. In this way, the protrusions assist in bending the resilient attachment members 217 as the cover 204 is mounted on the body portion 202.

Figure 5:
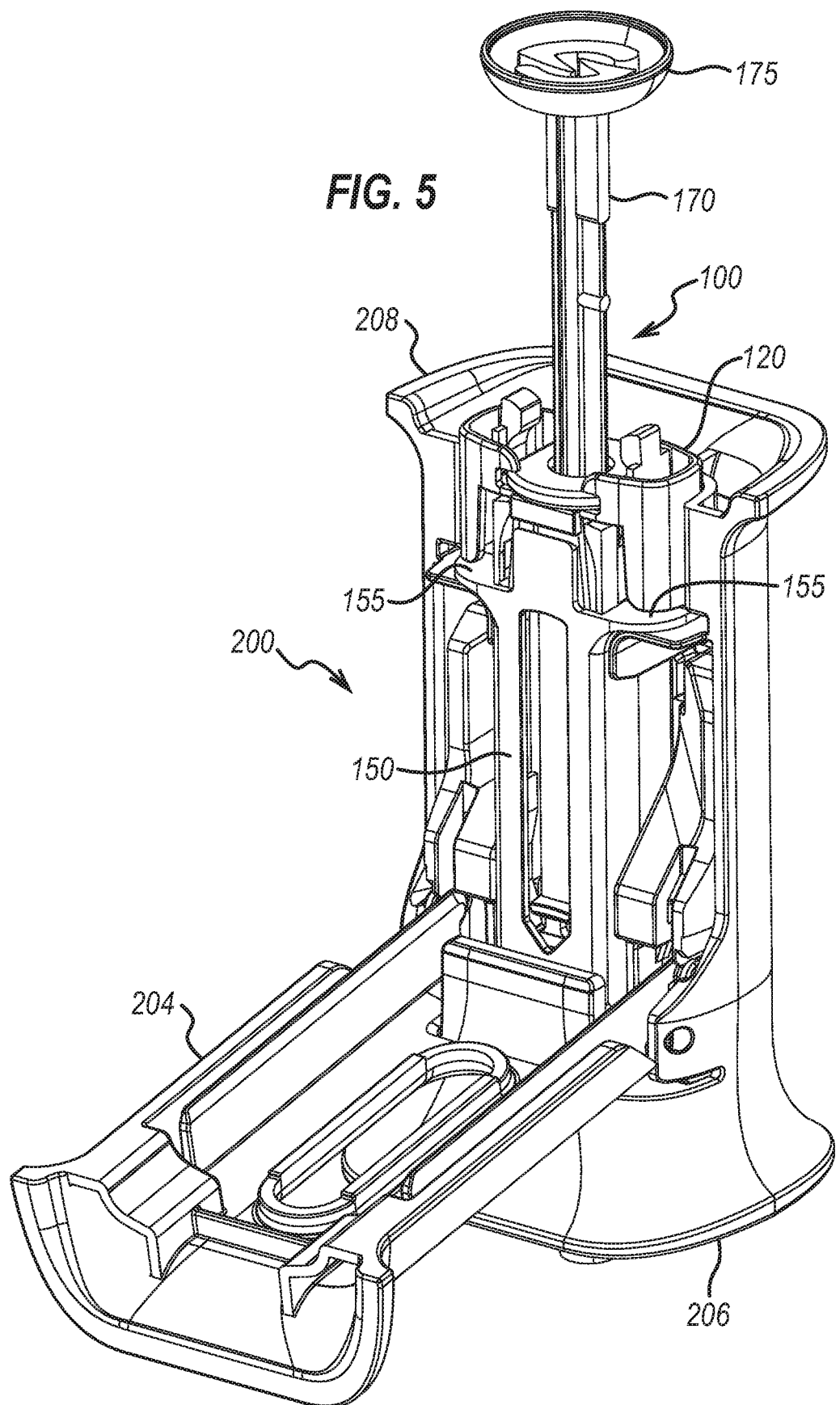
FIG. 5 is a perspective view of the accessory in the open configuration with the injection device within the accessory.

The body portion 202 comprises a recess 220 for receiving the injection device 100. FIG. 5 illustrates the injection device 100 positioned within the recess 220 with the length of the safety shield 150 positioned longitudinally within the recess 220. Referring back to FIG. 4, the body portion 202 also comprises a slot 222. The length of the slot 222 is arranged perpendicular to the longitudinal axis of the accessory 200. The slot 222 is adapted to receive the flanges 155 of the injection device 100, as illustrated in FIG. 5.

Figure 6:
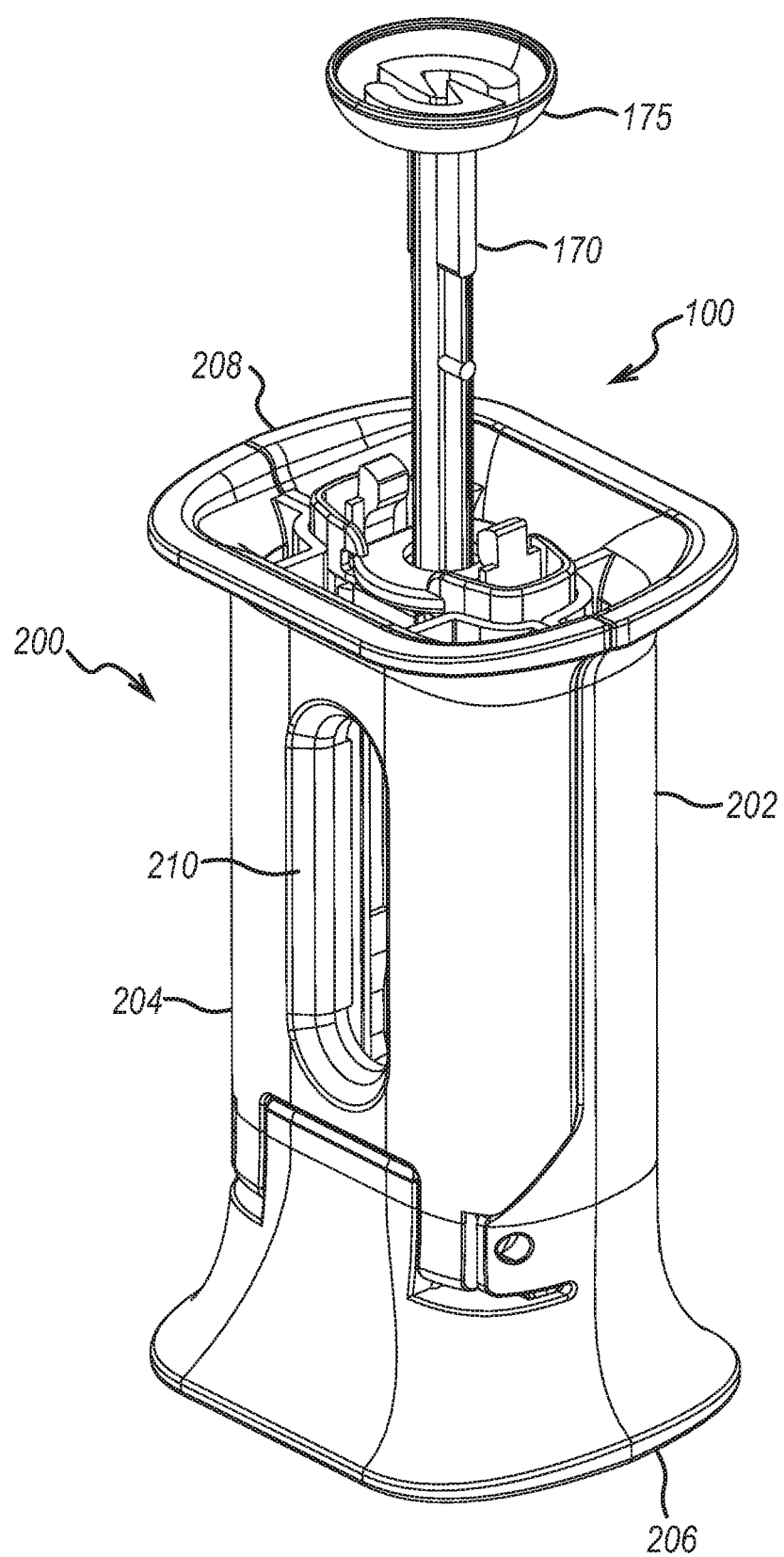
FIG. 6 is a perspective view of the accessory in the closed configuration with the injection device within the accessory.

When the cover 204 is in the open position, the recess 220 and slot 222 are exposed in order to receive the injection device 100. Specifically, the recess 220 receives the safety shield 150, and the slot 222 receives the flanges 155. Once the injection device 100 has been positioned in the recess 220 and the slot 222, the cover 204 is moved from the open position to the closed position, as illustrated in FIG. 6. The injection device 100 and accessory 200 are now ready for an injection to be administered. The user is able to place the accessory 200 containing the injection device on an injection site, for instance on the skin, and actuate the actuation surface 175 with one hand in order to administer the injection in a safe, simple and reliable manner.

When the cover 204 is in the closed position, the cover 204 closes the recess 220 and the slot 222 in order to hold the injection device 100 in the body portion 202. When the injection device 100 is held within the accessory 200 by the cover 204 and the body portion 202, the injection device 100 is visible through each window 210 provided on each face of the accessory 200. This allows the user to inspect the contents of the syringe prior to administering an injection.

Referring to FIGS. 4 and 5, the slot 222 is shaped to resist the flanges 155 from moving towards the distal end 206 of the accessory 200, or in other words the slot 222 is shaped to stop the flanges 155 moving distally. The slot 222 is also shaped to resist the flanges 155 from moving towards the proximal end 208 of the accessory 200, or in other words the slot 222 is shaped to stop the flanges 155 moving proximally. However, the slot 222 is shaped to allow the syringe sheath 120 of the injection device 100 to move proximally relative to the body portion 202. This allows the injection device 100 to move from the pre-injection position to the locked-out position, as described above. In this specific example, there is a cavity formed in the body portion 202 and the cover 204 through which the syringe sheath is allowed to move. However, the width of this cavity is sized such that the flanges 155 cannot move through the cavity, and thus the flanges 155 are retained in the slot 222 while the cover 204 is in the closed position.

Referring back to FIG. 3, the body portion 202 and the cover 204 are coupled together in order to form a pair of opposing sides. The right side 212 is illustrated in FIG. 3; the opposing left side is not shown but is a mirror image of the right side 212. The accessory 200 comprises a pair of opposing faces. The front face 214 is illustrated in FIG. 3; the opposing back face is not shown. The opposing faces each have a similar surface area and each have a larger surface area then each opposing side. The cover 204 forms part of the front face 214, and the body portion 202 forms the back face. The faces and the sides connect the distal end 206 of the accessory 200 with the proximal end 208 of the accessory 200.

The injection device 100 is positioned in the recess 220 by lowering the injection device 100 into the recess 220 at an angle. The direction in which the injection device 100 is moved towards the accessory 200 in order for the injection device 100 to be positioned in the recess 220 has a component in a direction perpendicular to the longitudinal axis of the accessory 200 and a component in a direction parallel with the longitudinal axis of the accessory 200. This direction extends towards the back face of the body portion 202. Specifically, the slot 222 and the recess 220 each have an open face that is parallel with the faces of the accessory 200 into which the injection device 100 is lowered. Since the faces of the accessory 200 have a larger surface area than the sides, this presents a wider area for a user to aim for when positioning the injection device 100 in the accessory 200. This allows a user to position the injection device 100 more easily, particularly for users with dexterity issues.

Referring to FIG. 4, the slot 222 comprises a pair of distal abutment portions 224 on each side of the body portion 202. The distal abutment portions 224 are fixed to the body portion 202, and each one of the distal abutment portions 224 resists a respective one of the flanges 155 from moving distally. The distal abutment portions 224 are each integrally formed with the body portion 202 which provides a secure connection that is simple to manufacture. However, the body portion 202 may be a modular part where the distal abutment portions 224 are removable from the body portion 202. Each distal abutment portion 224 has a flat upper surface which extends into a curved lower surface. This reflects the shape of the outside surface of the lower part of the flange, which assists in firmly securing the injection device 100 in the body portion 202.

The slot 222 also comprises a pair of proximal abutment portions 226. The proximal abutment portions 226 are fixed to the body portion 202, and each one of the proximal abutment portions 226 resists a respective one of the flanges 155 from moving proximally. The proximal abutment portions 226 are each integrally formed with the body portion 202 which provides a secure connection that is simple to manufacture. However, the body portion 202 may be a modular part where the proximal abutment portions 226 are removable from the body portion 202. Each proximal abutment portion 226 has a flat lower surface for interacting with an upper surface of a respective one of the flanges 155. The proximal abutment portions 226 are spaced apart from one another in order to form the cavity through which the syringe sheath 120 is allowed to travel.

Referring to FIG. 4, there is a cover slot 228 in the cover 204. The cover slot 228 is arranged to hold the flanges 155 when the cover 204 is moved from the open position illustrated in FIG. 4 to the closed position illustrated in FIG. 6. The cover slot 228 is shaped in order to resist the flanges 155 from moving towards the distal end 206 of the accessory 200 when the cover 204 is in the closed position, or in other words the cover slot 228 is shaped to stop the flanges 155 moving distally. The cover slot 228 is also shaped to resist the flanges 155 from moving towards the proximal end 208 of the accessory 200, or in other words the cover slot 228 is shaped to stop the flanges 155 moving proximally. However, the cover slot 228 is shaped to allow the syringe sheath 120 of the injection device 100 to move proximally relative to the body portion 202. This allows the injection device 100 to move from the pre-injection position to the locked-out position, as described above. In this specific example, the cover slot 228 co-operates with the slot 222 in the body portion 202 to form the cavity through which the syringe sheath 120 is allowed to move. However, the width of the cavity is sized such that the flanges 155 cannot move through the cavity, and thus the flanges 155 are retained in the cover slot 228 while the cover 204 is in the closed position.

The cover slot 228 also comprises a pair of distal abutment portions 230 on each side of the cover 204. The distal abutment portions 230 are fixed to the cover 204, and each one of the distal abutment portions 230 resists a respective one of the flanges 155 from moving distally. The distal abutment portions 230 are each integrally formed with the cover 204 which provides a secure connection that is simple to manufacture. However, the cover 204 may be a modular part where the distal abutment portions 230 are removable from the cover 204. As shown in the FIG. 4, each distal abutment portion 230 comprises a rib that extended along the length of the cover 204, thus providing structural support to the cover 204.

The cover slot 228 also comprises a pair of proximal abutment portions 232. The proximal abutment portions 232 are fixed to the cover 204, and each one of the proximal abutment portions 232 resists a respective one of the flanges 155 from moving proximally. The proximal abutment portions 232 are each integrally formed with the cover 204 which provides a secure connection that is simple to manufacture. However, the cover 204 may be a modular part where the proximal abutment portions 232 are removable from the cover 204.

Figure 7:
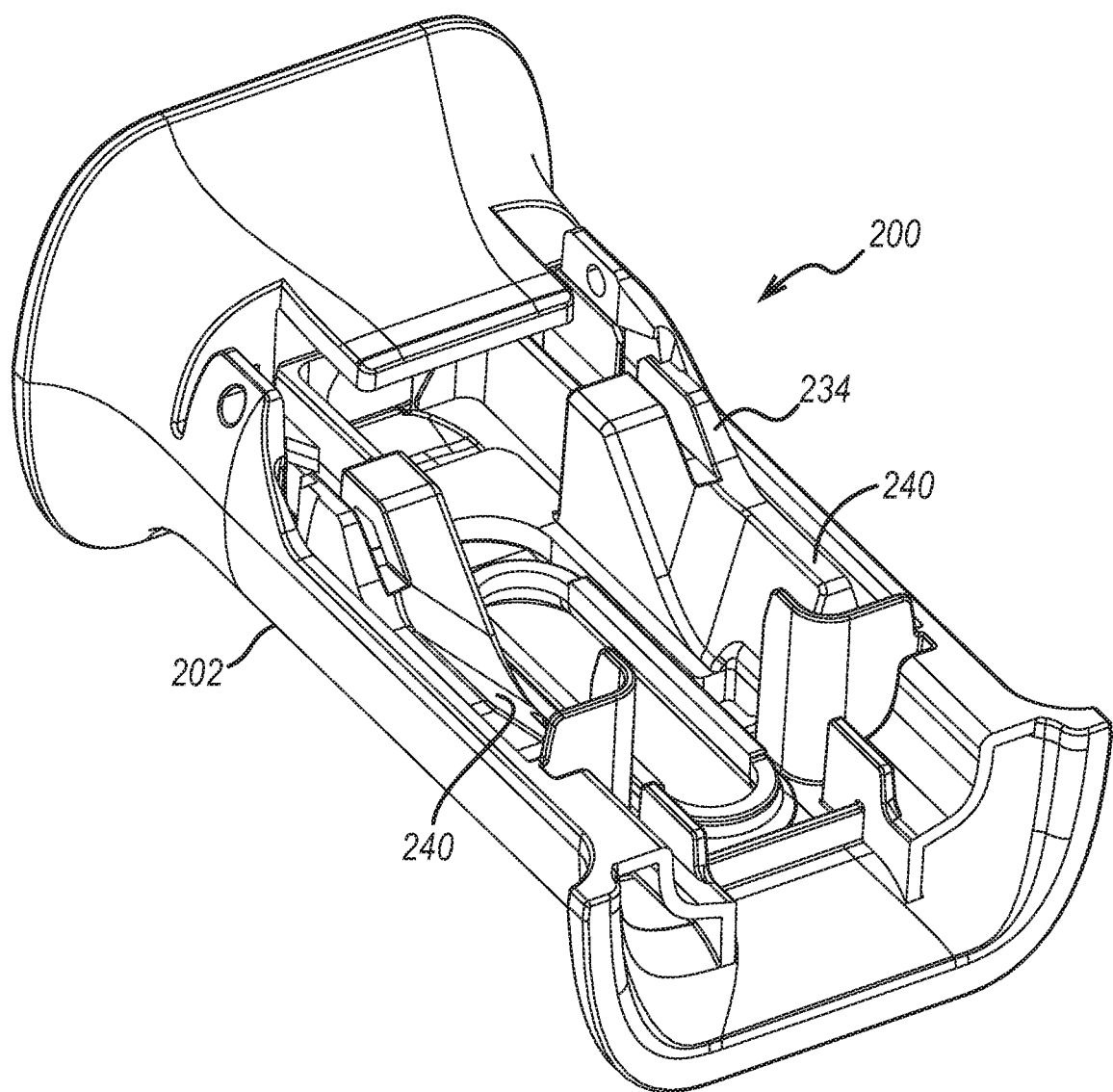
FIG. 7 is an internal view of the accessory without the injection device and a cover.
Figure 8:
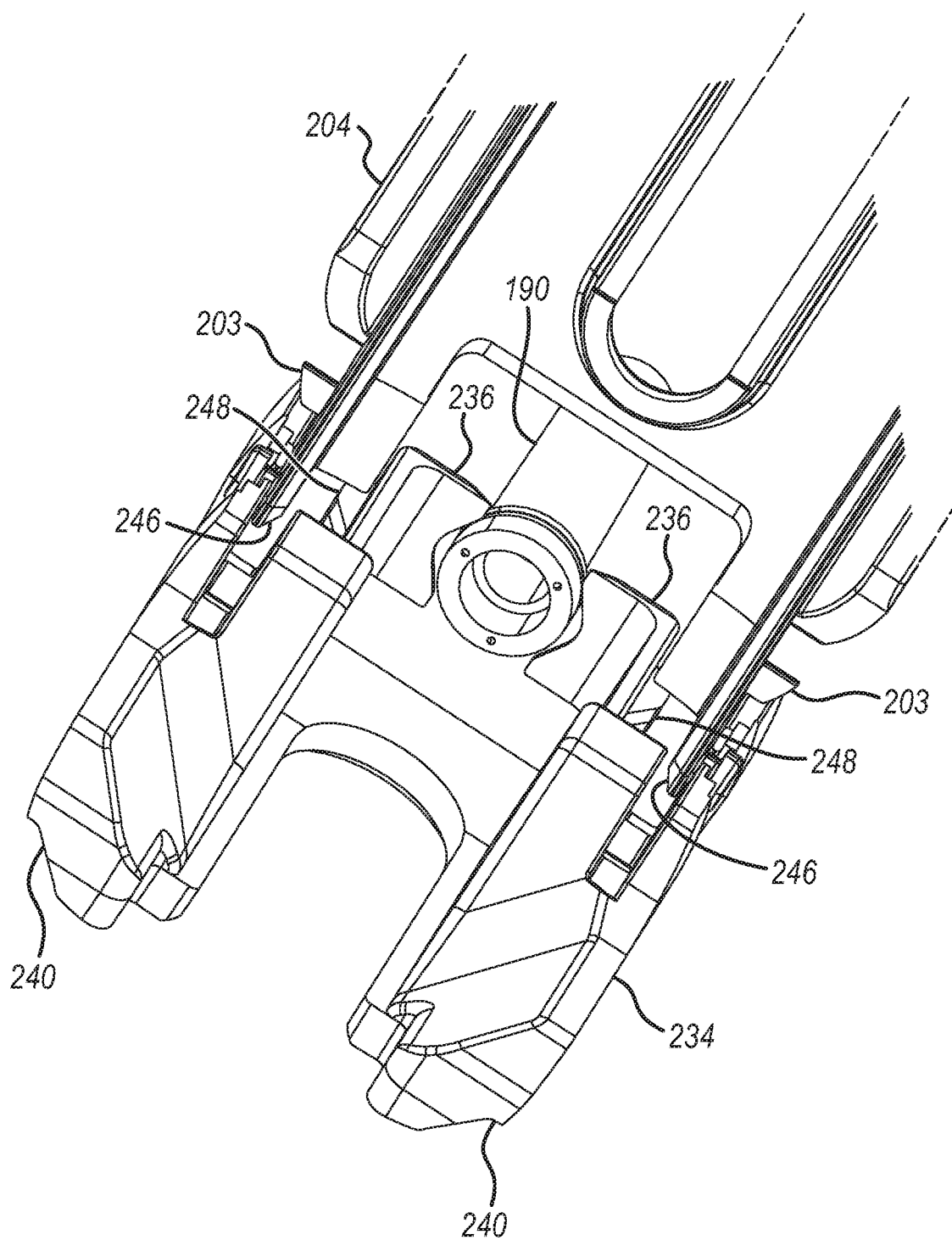
FIG. 8 is an enlarged perspective view of a cap remover and the cover of the accessory in an open position with a body portion not shown.

Referring to FIGS. 7 and 8, the accessory 200 comprises a cap remover 234 for removing the needle cap 190 from the injection device 100. The cap remover 234 comprises a grip which, in this example, comprises a pair of moveable elements 236 each having a gripping end for interacting with the needle cap 190. Each one the gripping ends is shaped to correspond with the outside surface of the needle cap 190. Each gripping end has a concave end for interfacing with the cylindrical outer shape of the needle cap 190. In this example, the moveable elements 236 are integrally formed with the cap remover 234. However, the moveable element 236 may be provided as separate components that bend, or rotate, relative to the cap remover 234. For instance, each moveable element 236 may be mounted on the cap remover 234 about a pivot. The needle cap 190 may be a rigid needle cap or a non-rigid needle cap. The rigid needle cap may be formed of at least two components, for example it may comprise a rigid outer shell and an inner body which surrounds the needle 130 on the syringe 110 when in place. The inner body may be a pliable, resilient or flexible inner body. This inner body may be a rubber inner body. Alternatively, a non-rigid needle cap may be utilised, in which case the needle cap may be a single pliable, resilient or flexible body, for example it may be a rubberised needle boot. In the case of the non-rigid needle cap, the cap remover 234 is adapted to grip the non-rigid needle cap resiliently during cap removal, for example between the pair of moveable elements 236. Since the cap is non rigid, it deforms within the cap remover 234, particularly within the grip so that the grip is snug and tight, and thus cap removal is achieved reliably.

In this example, the cap remover 234 has an expanded configuration (as illustrated in FIG. 8), and a constricted configuration (not shown). In the expanded configuration, the cap remover 234 does not interact with the needle cap 190. In particular, the needle cap 190 can pass through, or by, the moveable element 236 when the cap remover 234 is in the expanded configuration, such as when the injection device 100 is inserted into the recess 220. In the constricted configuration, the cap remover 234 holds the needle cap 190 so that the cap remover 234 can remove the needle cap 190 from the injection device 100. In particular, the moveable elements 236 move towards one another in order for the cap remover 234 to assume the constricted configuration to grip the needle cap 190 via the gripping ends. When the cover 204 is in the open position, the cap remover 234 is in the expanded position. Closing the cover 204 causes the cap remover 234 to assume the constricted configuration as it slides forward to remove the needle cap 190. However, when the cover 204 is fully closed (as illustrated in FIG. 6) the cap remover 234 again assumes the expanded configuration in order to release the needle cap 190.

In this specific example, the grip has two configurations: the expanded configuration and the constricted configuration. However, in another example the grip may assume the constricted configuration by default. In this case, the grip holds the needle cap 190 when the injection device 100 is placed in the accessory 200 without having to be moved from the expanded configuration to the constricted configuration. This alternative may be simpler to manufacture. However, the grip with the expanded configuration allows the injection device 100 to be inserted into the accessory 200 without resistance from the grip. In another, the grip may comprise only one moveable element that pushes the needle cap towards a non-moveable element.

The cap remover 234 comprises a pair of guides 240 each arranged to sit within a track in the body portion 202. The cap remover 234 is arranged to slide within the tracks in the body portion 202.

Figure 9:
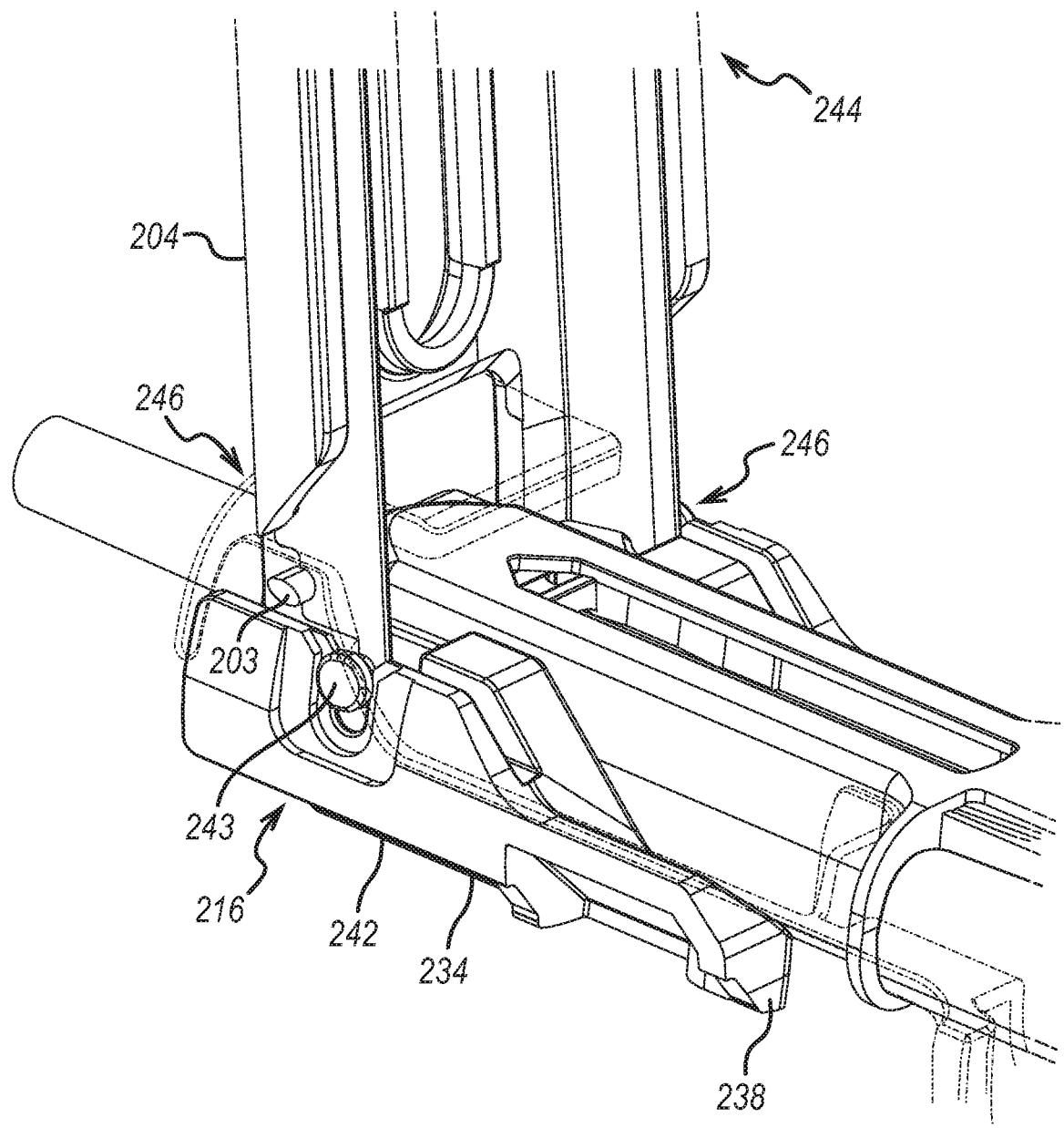
FIG. 9 is a further enlarged perspective view of the cap remover and the cover with the body portion not shown.
Figure 10:
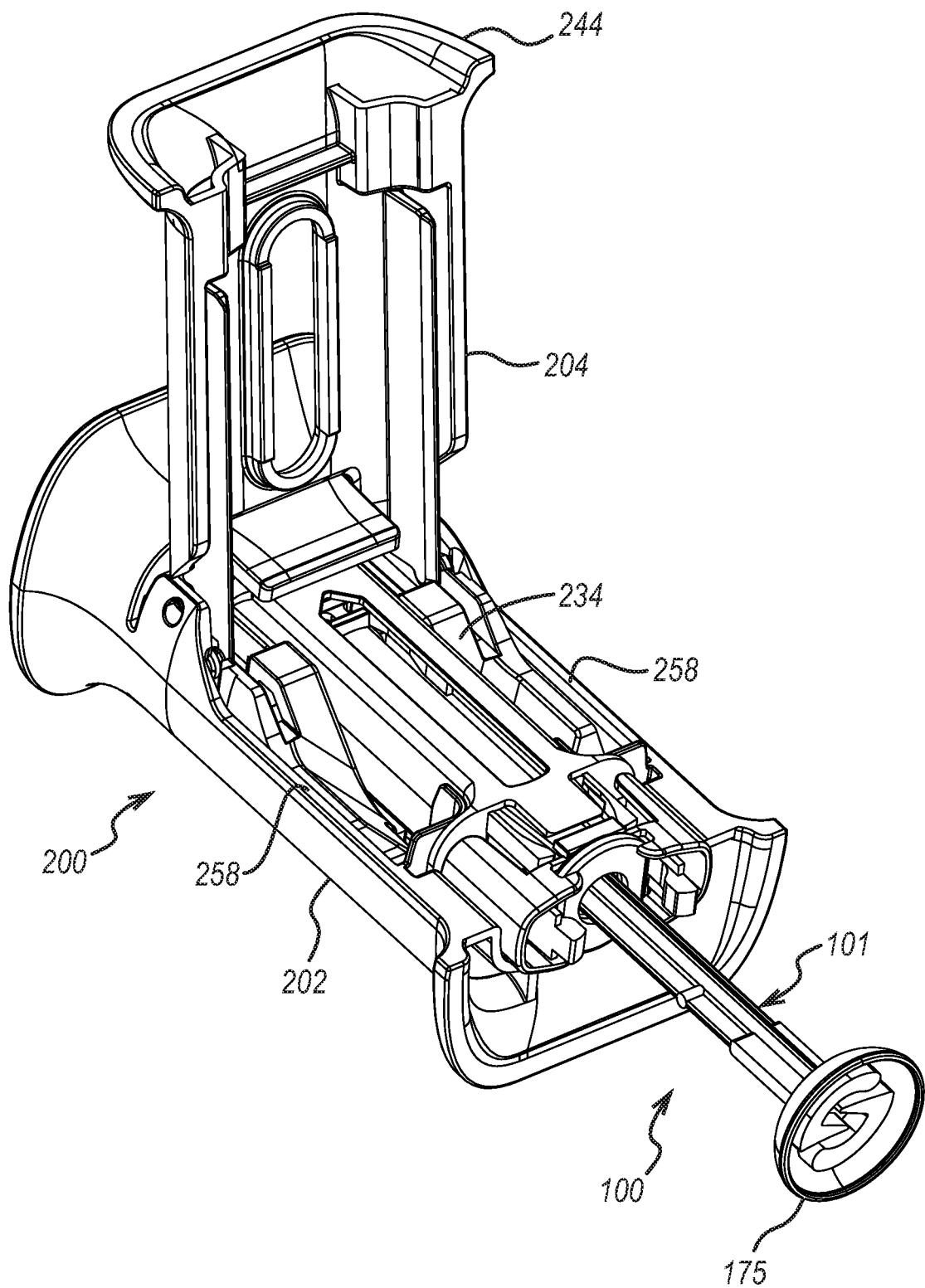
FIG. 10 is a further perspective view of the accessory in the open configuration with the injection device within the accessory.

Referring to FIGS. 9 and 10, the cap remover 234 comprises a pair of cap remover slots 242 each provided on one side of the cap remover 234. The cover 204 comprises a proximal end 244 that can be moved by a user in order to move the cover 204 from the open position to the closed position. The cover 204 also comprises a distal end 246 that is operably coupled to the cap remover 234 in order to move the cap remover 234 and the grip including the moveable elements 236 distally.

Figure 11:
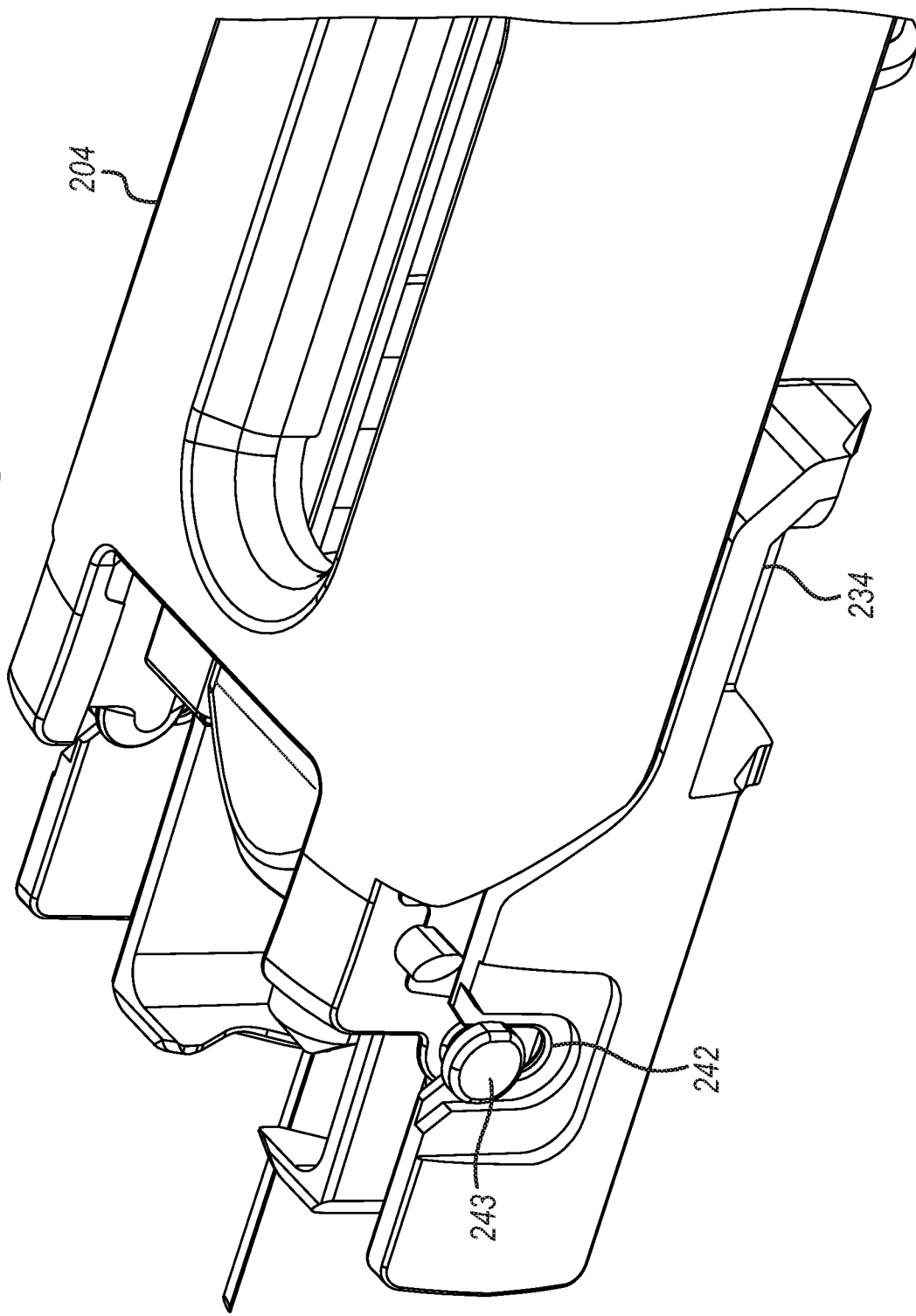
FIG. 11 is a perspective view of the cap remover and the cover in a closed positioned with the body portion not shown.

In this example, there are a pair of distal ends 246 of the cover 204 each comprising a cover cam 243 that sits within one of the cap remover slots 242. In this way, each distal end 246 interacts with a respective one of the cap remover slots 242 in order to translate the cap remover 234 distally, as the cover 204 is pivoted from the open position to the closed position. FIG. 11 illustrates the cover 204 in the closed position where the cap remover 234 has been moved distally.

Referring to FIG. 9, the cover 204 comprises a pair of distal extensions each extending distally away from each pivot 216. The distal end 246 and the cover cam 243 are provided on the distal extension. There is a pair of proximal extensions each corresponding to one of the distal extensions. Each proximal extension extends proximally away from each pivot 216, thus forming the two sides of the proximal end 244 of the cover 204.

Each proximal extension is longer than each distal extension. This assists in providing to mechanical advantage about the pivot 216 so that the cover 204 can be closed more easily. This is particularly important as this motion also moves the cap remover 234 distally in order to remove the needle cap 190.

Figure 12:
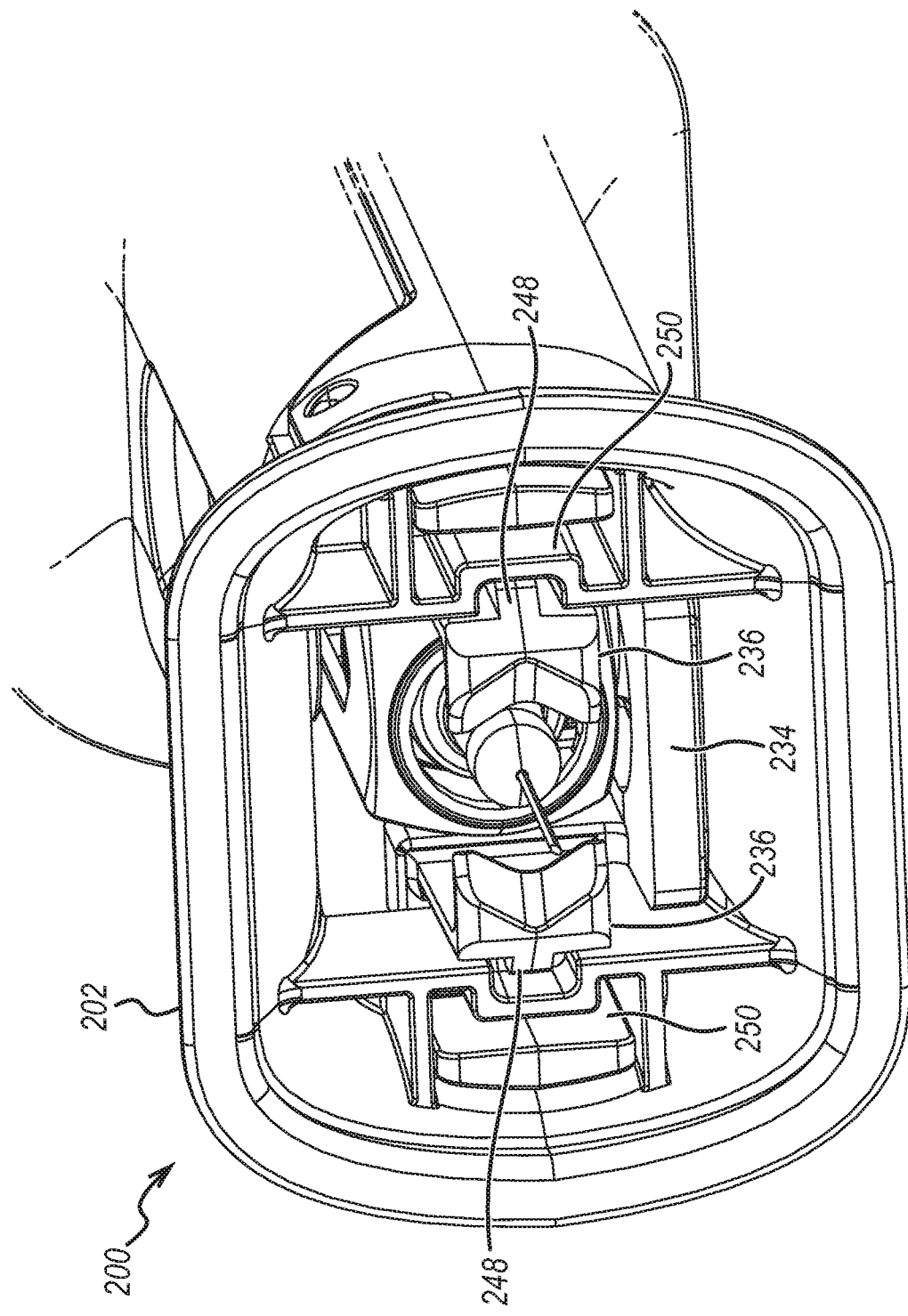
FIG. 12 is a perspective view of a base of the accessory.
Figure 13:
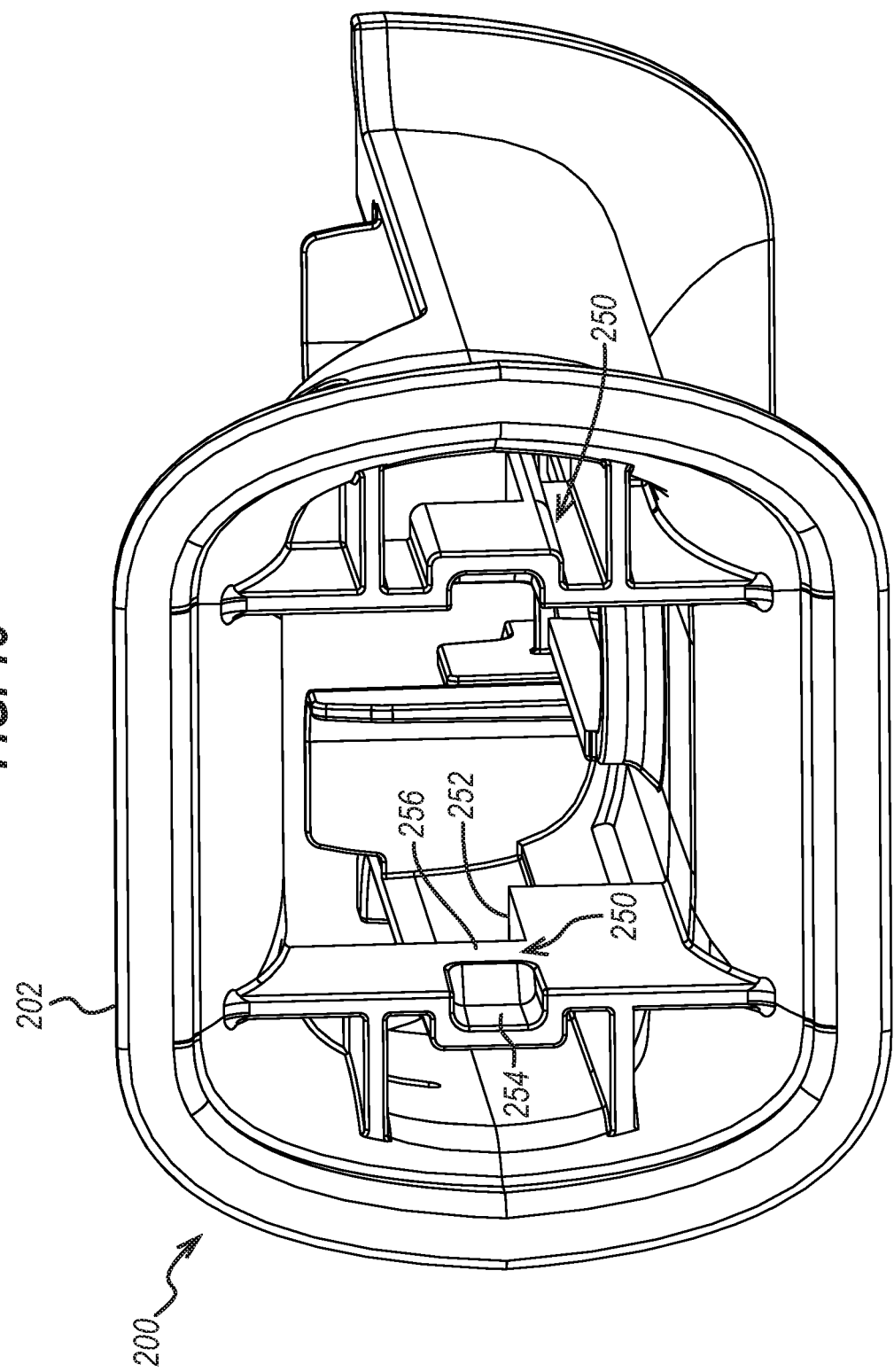
FIG. 13 is an internal view of the body portion of the accessory.
Figure 14:
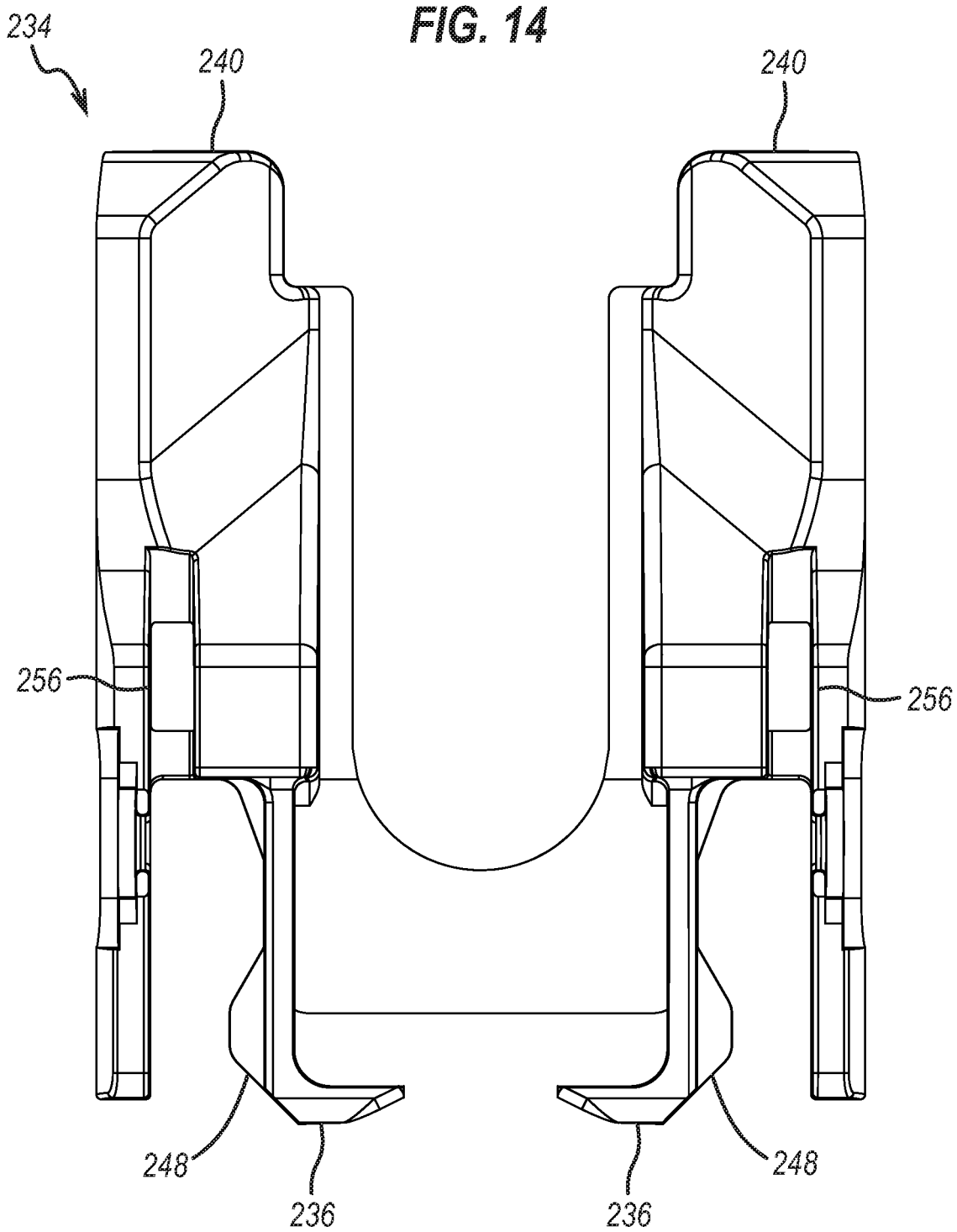
FIG. 14 is a plan view of the cap remover of the accessory.

Referring to FIGS. 8 and 14, each one of the moveable elements 236 of the grip is made of a flexible, resilient material. This allows the grip to move between the expanded configuration in which the needle cap 190 can pass between, or past, the grip and the constricted configuration in which the grip holds the needle cap 190 for removing the needle cap 190 from the injection device 100. There is a cap remover cam 248 on the outside surface of each one of the moveable elements 236. Each cap remover cam 248 interfaces with a cap remover cam surface 250 on the body portion 202, when the cap remover 234 is moved distally by the cover 204. The cap remover cam surfaces 250 are illustrated in FIGS. 12 and 13. The cap remover 234 also comprises a pair of receiver slots each adapted to receive at least a portion of the cover 204 when the cover 204 is in the closed position.

The cap remover cams 248 are forced into the cap remover cam surfaces 250 with the cap remover 234 advancing distally. This pushes the moveable elements 236 towards one another in order to move the grip from the expanded configuration into the constricted configuration. Thus, when the injection device 100 is within the recess 200, the moveable elements 236 grip the needle cap 190, and at the same time the cap remover 234 is moved distally, thus pulling the needle cap 190 distally and away from the injection device 100. This removes the needle cap 190 from the injection device 100.

Referring to FIGS. 12 and 13, each one of the cap remover cam surfaces 250 is shaped such that the grip moves from the expanded configuration, to the constricted configuration and back the expanded configuration as the cover 204 moves from the open position to the fully closed position. In this example, each one of the cap remover cam surfaces 250 has a proximal end 252 and a distal end 254 that do not interact with a respective one of the cap remover cams 248, and an intermediate section 256 that is positioned to interact with a respective one of the cap remover cams 248 in order to move the moveable element 236 as the cap remover 234 moves distally.

FIG. 8 illustrates the cover 204 in the fully open position in which the cam remover 234 is in the expanded configuration. FIG. 12 illustrates the cover 204 in the fully closed position in which the cam remover has reverted back to the expanded configuration from the constricted configuration, as the cover 204 is moved from the fully open to the fully closed position.

Figure 15:
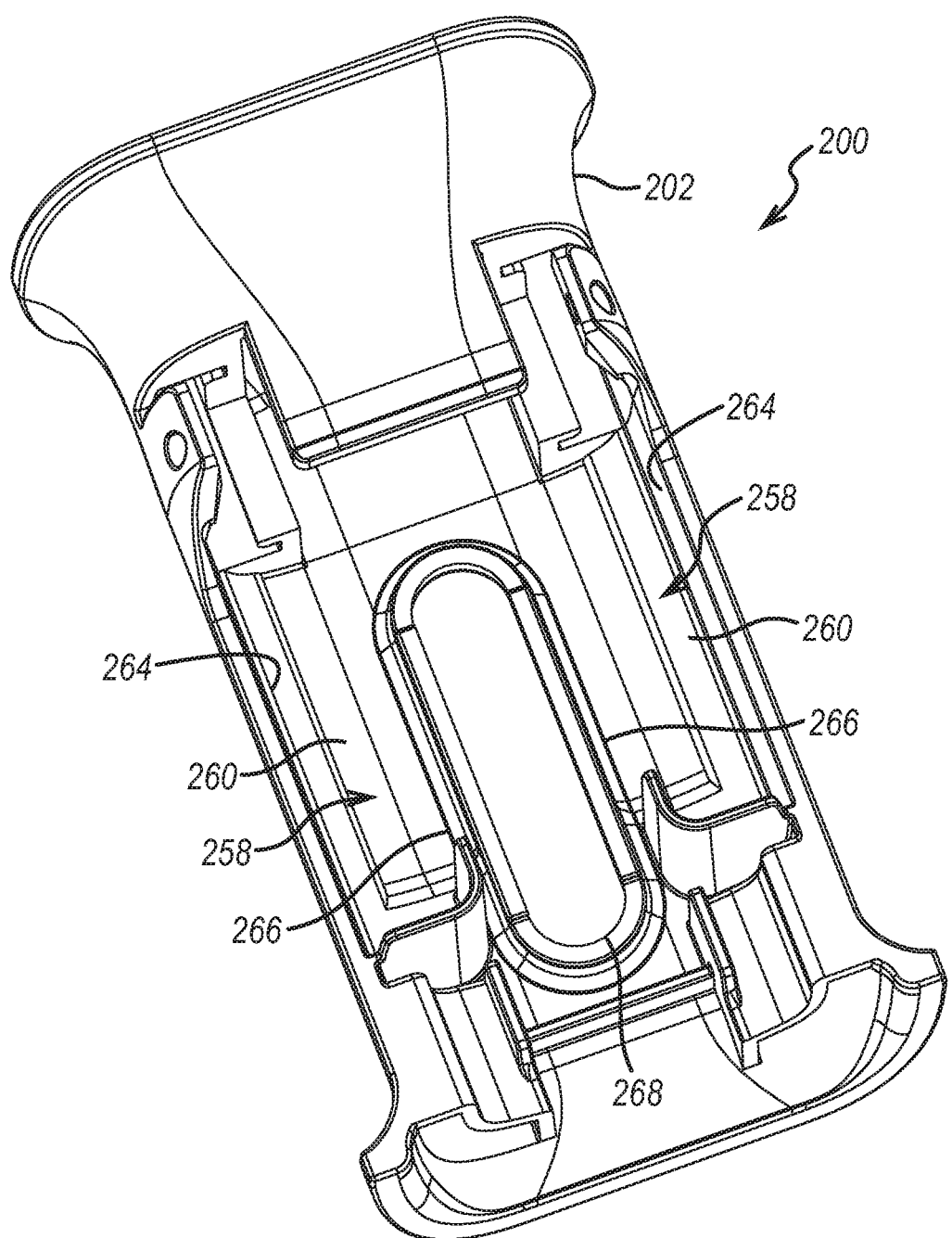
FIG. 15 is a further perspective view of the body portion.

Referring to FIG. 15, the body portion 202 comprises a pair of tracks 258 for receiving a respective guide 240 of the cap remover 234. Each track 258 is adapted such that when the injection device 100 is located in the body portion 202, the cap remover 234 is prevented from moving out of the track. This is illustrated in FIG. 10. Specifically, the injection device 100 holds the cap remover 234 in each track 258 when the injection device 100 is in the recess 220.

Each track 258 is configured such that when the injection device 100 is not located in the body portion 202, the cap remover 234 is allowed to move in a direction having a component perpendicular to the axial direction (i.e. the longitudinal direction that extends from the proximal end 208 to the distal end 206 of the accessory 200). However, when the injection device 100 is located in the body portion 202, the cap remover 234 is held against each track 258 by the injection device 100 such that the cap remover 234 can only slide axially with respect to the body portion 202.

As illustrated in FIG. 7, each track exposes at least a portion of the cap remover 234 so that the injection device 100 at least partially holds the cap remover 234 within the tracks 258 when the injection device 100 is positioned in the recess 220. As illustrated in FIG. 10, the tracks 258 expose the cap remover 234 in that each track 258 does not comprise means adapted to contact an upper surface of the cap remover 234. In other words, the body portion 202 does not have a lip or other such retention means for holding the cap remover 234 in the body portion 202. Instead, the injection device 100 holds the cap remover 234 in the tracks 258. In particular, the cap remover 234 directly contacts the injection device 100 when the injection device 100 is positioned within the recess 220. This simplifies the design of the accessory 200.

Referring to FIG. 15, each track 258 comprises a base 260 and a pair of side walls 264, 266 adapted to guide respective side surfaces of the cap remover 234. In this example, the pair of side walls 264, 266 are integrally formed with the body portion 202. However, in another example one or both of side walls 264, 266 are separate components to the body portion 202. A first one of side walls 266 of each track 258 defines a wall of a window 268 through which the injection device 100 is visible when the injection device 100 is within the accessory 200. A second one of the side walls 264 of each track 258 defines an external side wall of the accessory 200. The base 260 and/or the side walls 264, 266 of each track 248 are integrally formed with the body portion 202.

The features of the accessory 200 described above provide an accessory 200 that is inexpensive, simple and easy to use. In addition, it is possible to operate the accessory 200 with one hand in order to administer an injection with the injection device 100.

In use, the injection device as described above might be used to contain and deliver substances such as: antibodies (such as monoclonal antibodies, ustekinumab, golimumab, infliximab, guselkumab, sirukumab, adalimumab, rituximab, tocilizumab, certolizumab, certolizumab pegol, sarilumab, secukinumab, ixekizumab or biosimilar versions thereof), etanercept, abatacept, anakinra, epoetin alfa, darbepoetin alfa, epoetin beta-methoxy polyethylene glycol, peginesatide, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity. In addition to these substances, any medicament contained within the injection device may also include other substances, such as inactive ingredients, as a skilled person would appreciate. It will of course be understood by the person skilled in the art that particular substances are efficacious for use in the treatment or prevention of particular conditions, as is well known in the art. For instance, it is known that antiallergics are efficacious for use in the treatment or prevention of allergies; antihistamines are efficacious for use in the treatment or prevention of hay fever; anti-inflammatories are efficacious for use in the treatment or prevention of inflammation; and so on. Accordingly, any selection of one or more substances listed herein or in the claims for use in the treatment or prevention of one or more conditions for which those substance(s) are known to be efficacious is envisaged. In a particular example, however, golimumab is known to be efficacious for use in the treatment or prevention of one or more of rheumatoid arthritis, psoriatic arthritis, ankylosing spondylitis or ulcerative colitis, or any combination of rheumatoid arthritis, psoriatic arthritis, ankylosing spondylitis and ulcerative colitis, or all of rheumatoid arthritis, psoriatic arthritis, ankylosing spondylitis and ulcerative colitis.

Golimumab may optionally be used in combination with one or more inactive ingredients such as any or all of L-histidine, L-histidine monohydrochloride monohydrate, sorbitol, polysorbate 80, and water. Golimumab may be present in a composition in which golimumab is the only active ingredient. For example, golimumab may be administered as SIMPONI®.

The term "comprising" encompasses "including" as well as "consisting" e.g. a composition "comprising" X may consist exclusively of X or may include something additional e.g. X+Y. Unless otherwise indicated each embodiment as described herein may be combined with another embodiment as described herein. In the specific examples described to above, pairs of certain components are provided in order to achieve certain functions. However, it is possible to achieve these functions using at least one of these components.

It will be understood that the benefits and advantages described above may relate to one embodiment or may relate to several embodiments. The embodiments are not limited to those that solve any or all of the stated problems or those that have any or all of the stated benefits and advantages. Any reference to 'an' item refers to one or more of those items.

It will be understood that the above description of a preferred embodiment is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this invention.

The invention claimed is:

1. An accessory for an injection device having a needle cap, the accessory comprising:
   a body portion comprising a recess adapted to receive the injection device;
   a cover coupled to the body portion, the cover pivotally moveable between an open position in which the recess is exposed to receive the injection device, and a closed position in which the cover at least partially closes the recess to hold the injection device in the body portion; and
   a cap remover comprising a grip, the cap remover having an expanded configuration in which the needle cap can pass between the grip, and a constricted configuration in which the grip holds the needle cap to at least partially remove the needle cap from the injection device;
   wherein the cover and the cap remover are operably coupled to one another whereby when the cover is moved from the open position towards the closed position the cap remover moves from the expanded configuration to the constricted configuration, and
   wherein the grip comprises at least one moveable element configured to hold the needle cap when the cap remover is in the constricted configuration and being offset from the needle cap when the cap remover is in the expanded configuration, the at least one moveable element being formed from a flexible, resilient material that allows the at least one moveable element to move between the constricted configuration in which the grip holds the needle cap and the expanded configuration in which the needle cap can pass between the grip.

2. The accessory of claim 1, wherein the cap remover is arranged to revert back to the expanded configuration when the cover reaches the closed position to release the needle cap.

3. The accessory of claim 1, further comprising at least one cap remover cam arranged to interact with at least one cap remover cam surface so as to move the cap remover from the expanded configuration to the constricted configuration.

4. The accessory of claim 3, wherein the at least one cap remover cam is coupled to, or provided on, the at least one moveable element.

5. The accessory of claim 3, wherein the cap remover cam surface is coupled to, or provided on, the body portion.

6. The accessory of claim 3, wherein the at least one cap remover cam surface is arranged to interact with the cap remover cam in order to move the cap remover from the expanded configuration, to the constricted configuration and back to the expanded configuration as the cap remover cam moves over and past the cap remover cam surface.

7. The accessory of claim 3, wherein the at least one cap remover cam and the at least one cap remover cam surface are offset from one another when the cover is in the open position.

8. The accessory of claim 3, wherein movement of the cover from the open position to the closed position causes the cap remover cam to move into engagement with the cap remover cam surface, so that the cap remover moves from the expanded configuration to the constricted configuration.

9. The accessory of claim 1, wherein the grip comprises at least one gripping end that is shaped to correspond with an outside surface of the needle cap.

10. The accessory of claim 1, wherein the at least one moveable element comprises a pair of moveable elements configured to hold the needle cap when the cap remover is in the constricted configuration and being offset from the needle cap when the cap remover is in the expanded configuration.

11. The accessory of claim 10, wherein each one of the pair of moveable elements is formed from a flexible, resilient material that allows each moveable element to move between the constricted configuration in which the grip holds the needle cap and the expanded configuration in which the needle cap can pass between the grip.

12. The accessory of claim 10, further comprising a pair of cap remover cams each arranged to interact with one of a pair of respective cap remover cam surfaces so as to move the cap remover from the expanded configuration to the constricted configuration.

13. The accessory of claim 12, wherein each cap remover cam is coupled to, or provided on, a respective one of the moveable elements.

14. The accessory of claim 12, wherein each cap remover cam surface is coupled to, or provided on, the body portion.

15. The accessory of claim 12, wherein the cap remover cam surfaces are arranged to move the cap remover from the expanded configuration, to the constricted configuration and back to the expanded configuration as the cap remover cams move over and past each respective cap remover cam surface.

16. The accessory of claim 12, wherein each cap remover cam and the corresponding cap remover cam surface are offset from one another when the cover is in the open position, so that the cap remover cam and the cap remover do not interface with one another.

17. The accessory of claim 12, wherein movement of the cover from the open position to the closed position causes each respective cap remover cam to move into engagement with the corresponding cap remover cam surface, so that the cap remover moves from the expanded configuration to the constricted configuration.

18. The accessory of claim 1, wherein the grip comprises a pair of gripping ends each shaped to correspond with an outside surface of the needle cap.

19. An accessory for an injection device having a needle cap, the accessory comprising:
   a body portion comprising a recess adapted to receive the injection device;
   a cover coupled to the body portion, the cover pivotally moveable between an open position in which the recess is exposed to receive the injection device, and a closed position in which the cover at least partially closes the recess to hold the injection device in the body portion; and
   a cap remover comprising a grip, the cap remover having an expanded configuration in which the needle cap can pass between the grip, and a constricted configuration in which the grip holds the needle cap to at least partially remove the needle cap from the injection device,
   wherein the cover and the cap remover are operably coupled to one another whereby when the cover is moved from the open position towards the closed position the cap remover moves from the expanded configuration to the constricted configuration, and
   wherein the grip comprises at least one moveable element configured to hold the needle cap when the cap remover is in the constricted configuration and being offset from the needle cap when the cap remover is in the expanded configuration, the at least one moveable element being configured to bend between the constricted configuration in which the grip holds the needle cap and the expanded configuration in which the needle cap can pass between the grip.

20. The accessory of claim 19, wherein the at least one moveable element comprises a pair of moveable elements configured to hold the needle cap when the cap remover is in the constricted configuration and being offset from the needle cap when the cap remover is in the expanded configuration, each one of the pair of moveable elements being configured to bend between the constricted configuration in which the grip holds the needle cap and the expanded configuration in which the needle cap can pass between the grip.

21. A system for administering an injection, the system comprising: the injection device having the needle cap; and the accessory of claim 1.

22. The system of claim 21, wherein the injection device contains a substance selected from the group consisting of:
antibodies (such as monoclonal antibodies, ustekinumab, golimumab, infliximab, guselkumab, sirukumab, adalimumab, rituximab, tocilizumab, certolizumab, certolizumab pegol, sarilumab, secukinumab, ixekizumab or biosimilar versions thereof), etanercept, abatacept, anakinra, epoetin alfa, darbepoetin alfa, epoetin betamethoxy polyethylene glycol, peginesatide, hormones, antitoxins, substances for the control of pain, substances for the control of thrombosis, substances for the control or elimination of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying antirheumatic drugs, erythropoietin, or vaccines, for use in the treatment or prevention of rheumatoid arthritis, psoriatic arthritis, ankylosing spondylitis, ulcerative colitis, hormone deficiencytoxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

23. An accessory for an injection device having a needle cap, the accessory comprising:
a body portion comprising a recess configured to receive the injection device;
a cover coupled to the body portion, the cover pivotally moveable between an open position in which the recess is exposed to receive the injection device, and a closed position in which the cover at least partially closes the recess to hold the injection device in the body portion; and
a cap remover comprising a grip, the cap remover having an expanded configuration in which the needle cap can pass between the grip, and a constricted configuration in which the grip holds the needle cap to at least partially remove the needle cap from the injection device;
wherein the cover and the cap remover are operably coupled to one another whereby, when the cover is moved from the open position towards the closed position, the cap remover moves from the expanded configuration to the constricted configuration and from the constricted configuration to the expanded configuration,
wherein the grip comprises at least one moveable element configured to i) move towards the needle cap along an inward direction along a line of trajectory to the constricted configuration to hold the needle cap, and ii) reverse direction to move from the constricted configuration away from the needle cap back along the line of trajectory along an outward direction, opposite the inward direction, to the expanded configuration to release the needle cap.

24. The accessory of claim 23, wherein the at least one moveable element comprises a pair of movable elements, each of the movable elements configured to move i) towards the other movable element along an inward direction to the constricted configuration to hold the needle cap, and ii) away from the other movable element along an outward direction, opposite the inward direction, to the expanded configuration to release the needle cap.

25. The accessory of claim 23, wherein the inward and outward directions are perpendicular to a longitudinal axis of the accessory.

26. The accessory of claim 23, wherein the cover and the cap remover are operably coupled to one another such that, when the cover is moved from the open position towards the closed position the cap remover moves from the expanded configuration to the constricted configuration, and when the cover is further moved towards the closed position, the cap remover moves from the constricted configuration to the expanded configuration.

\* \* \* \* \*